(12) United States Patent
O'Mahony et al.

(10) Patent No.: US 10,724,984 B2
(45) Date of Patent: Jul. 28, 2020

(54) SP3 SUBSTITUTED CARBON ELECTRODE TOC ANALYSIS USING METALLIC CATALYST

(71) Applicant: Hach Company, Loveland, CO (US)

(72) Inventors: Seamus O'Mahony, Cork (IE); Vishnu Vardhanan Rajasekharan, Fort Collins, CO (US)

(73) Assignee: HACH COMPANY, Loveland, CO (US)

( * ) Notice: Subject to any disclaimer, the term of this patent is extended or adjusted under 35 U.S.C. 154(b) by 190 days.

(21) Appl. No.: 15/663,732

(22) Filed: Jul. 29, 2017

(65) Prior Publication Data

US 2019/0033249 A1 Jan. 31, 2019

(51) Int. Cl.
*G01N 27/416* (2006.01)
*G01N 27/30* (2006.01)
*G01N 33/18* (2006.01)

(52) U.S. Cl.
CPC ......... *G01N 27/416* (2013.01); *G01N 27/308* (2013.01); *G01N 33/1846* (2013.01)

(58) Field of Classification Search
None
See application file for complete search history.

(56) References Cited

U.S. PATENT DOCUMENTS

| 3,854,881 | A | * | 12/1974 | Cohen | ................. | G01N 31/005 |
| | | | | | | 422/79 |
| 2005/0226774 | A1 | * | 10/2005 | Kounaves | .......... | G01N 33/1846 |
| | | | | | | 422/80 |

(Continued)

FOREIGN PATENT DOCUMENTS

| CA | 2642160 | 8/2007 |
| EP | 1640715 | 3/2006 |

(Continued)

OTHER PUBLICATIONS

Joowook Lee et al., "Electrochemical Oxidation of Mn2+ on Boron-Doped Diamond Electrodes with Bi3+ Used as an Electron Transfer Mediator", Journal of The Electrochemical Society, 2004, 6 pages, The Electrochemical Society, Inc.

(Continued)

*Primary Examiner* — Eli S Mekhlin
(74) *Attorney, Agent, or Firm* — Ference & Associates LLC

(57) ABSTRACT

An embodiment provides a method for oxidizing organic carbon, including: introducing, in a reaction chamber of a total organic carbon analyzer, a fluid sample comprising organic carbon, wherein the reaction chamber includes an electrochemical cell and wherein the electrochemical cell comprises an SP3 substituted solid carbon electrode doped with a conductivity elevating composition; applying, using a generator, a positive potential to the SP3 substituted carbon electrode, the positive potential being sufficient to oxidize organics in the fluid sample to produce carbonate and partially oxidized organics; introducing, in the reaction chamber, at least one acid reagent comprising a metallic catalyst, prior to or substantially simultaneously during the application of the positive potential to the SP3 substituted carbon electrode, that converts the carbonate and the partially oxidized species to carbon dioxide; and detecting, using at least one detector, the carbon dioxide produced by the oxidation. Other aspects are described and claimed.

8 Claims, 4 Drawing Sheets

(56) References Cited

U.S. PATENT DOCUMENTS

2006/0073605 A1* 4/2006 Horan ................. G01N 31/005
436/155
2015/0129435 A1* 5/2015 Franaszczuk .......... G01N 27/49
205/785.5

FOREIGN PATENT DOCUMENTS

WO     2013/172868     11/2013
WO     03/104765     12/2013

OTHER PUBLICATIONS

P. Canizares et al., "Electrochemical synthesis of ferrate using boron doped diamond anodes", ScienceDirect, Electrochemistry Communications, 2007, 5 pages, Elsevier.

International Searching Authority, Notification of Transmittal of the International Search Report and the Written Opinion of the International Searching Authority, or the Declaration, dated Oct. 22. 2018, 20 pages.

\* cited by examiner

SP3 SUBSTITUTED CARBON ELECTRODE TOC ANALYSIS USING METALLIC CATALYST

BACKGROUND

This application relates generally to carbon analysis techniques in aqueous samples and, more particularly, to the measurement of the Total Organic Carbon (TOC) present in said samples.

Ensuring water purity is critical in many applications, for example in municipalities that provide drinking water and in numerous other industries such as pharmaceuticals, chemicals and other manufacturing fields. The presence of organic compounds in the water may suggest a failure in filtration and/or other components and systems that, if left unchecked, can damage expensive industrial systems, impact product quality, be detrimental to public health, and even affect profit margins. As an example, drinking water quality will deteriorate if organics are present. The propensity for the formation of toxic carcinogens like trihalomethanes increased in the presence of organic contamination. Therefore, detecting the presence and concentration of organic contaminants in water samples is vital. TOC analysis is the measure of the level of organic molecules or contaminants in purified water and is often used as a non-specific indicator of water quality.

BRIEF SUMMARY

In summary, one embodiment provides a method for oxidizing organic carbon, comprising: introducing, in a reaction chamber of a total organic carbon analyzer, a fluid sample comprising organic carbon, wherein the reaction chamber includes an electrochemical cell and wherein the electrochemical cell comprises an SP3 substituted solid carbon electrode doped with a conductivity elevating composition; applying, using a generator, a positive potential to the SP3 substituted carbon electrode, the positive potential being sufficient to oxidize organics in the fluid sample to produce carbonate and partially oxidized organics; introducing, in the reaction chamber, at least one acid reagent comprising a metallic catalyst, prior to or substantially simultaneously during the application of the positive potential to the SP3 substituted carbon electrode, that converts the carbonate and the partially oxidized species to carbon dioxide; and detecting, using at least one detector, the carbon dioxide produced by the oxidation.

An embodiment provides a total organic carbon analyzer, comprising: a housing comprising: a reaction chamber, wherein the reaction chamber includes an electrochemical cell and wherein the electrochemical cell comprises a SP3 substituted carbon electrode doped with a conductivity elevating composition; and at least one detector; the total organic carbon analyzer being configured to: receive, in the reaction chamber, a fluid sample comprising organic carbon; apply a positive potential to the SP3 substituted carbon electrode, the positive potential being sufficient to oxidize organics in the fluid sample to produce carbonate and partially oxidized organics; introduce, in the reaction chamber prior to or substantially simultaneously during application of the positive potential to the SP3 substituted carbon electrode, at least one acid reagent comprising a metallic catalyst that converts the carbonate and the partially oxidized organics to carbon dioxide; and detect, using the at least one detector, the carbon dioxide produced by the oxidation.

An embodiment provides a product for analyzing total organic carbon in a sample, comprising: a storage device that stores code, the code being executable by a processor and comprising: code that introduces a fluid sample comprising organic carbon into a reaction chamber, wherein the reaction chamber includes an electrochemical cell and wherein the electrochemical cell comprises a SP3 substituted carbon electrode doped with a conductivity elevating composition; code that applies a positive potential to the SP3 substituted carbon electrode, the positive potential being sufficient to oxidize organics in the fluid sample to produce carbonate and partially oxidized organics; code that introduces, in the reaction chamber prior to or substantially simultaneously during application of the positive potential to the SP3 substituted carbon electrode, at least one acid reagent comprising a metallic catalyst that converts the carbonate and the partially oxidized organics to carbon dioxide; and code that detects the carbon dioxide produced by the oxidation.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
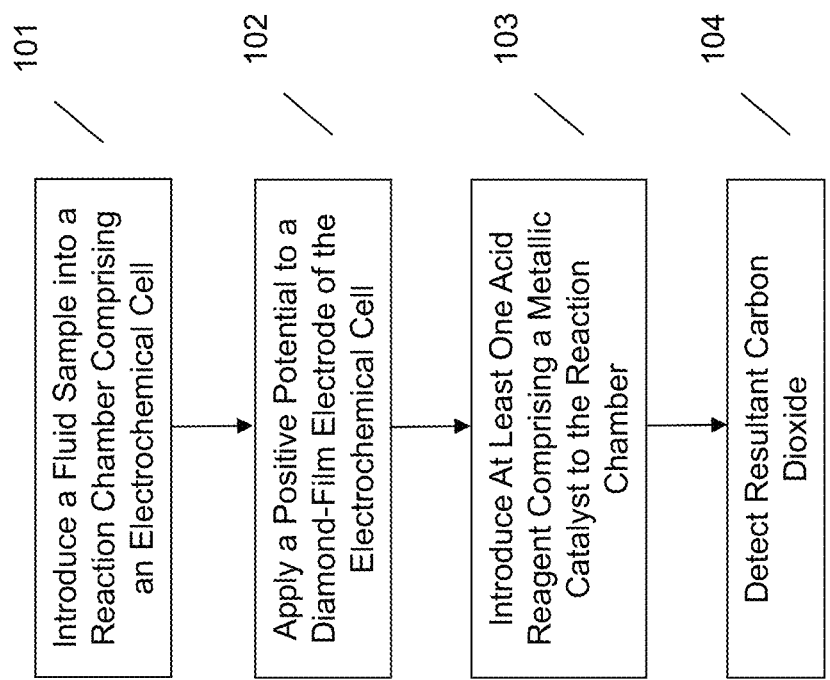
FIG. 1 illustrates an example method of detecting total organic carbon in a fluid sample.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

A variety of total organic carbon (TOC) methods and techniques exist today. However, many of the existing techniques require the use of hazardous reagents (e.g., strong acids and oxidizing agents, etc.) and are required to be performed in harsh environments (e.g., under ultraviolet light, in high temperature ovens, etc.) in order for the oxidation reactions to be properly executed. These issues have led to the development of safer and more cost-effective electrochemical devices that are capable of oxidizing organic carbon and determining TOC levels in aqueous solutions.

One such device, a TOC analyzer produced and distributed by O.I. Analytical (i.e., the 9210e On-line TOC Analyzer), utilizes a thin diamond-film electrode doped with boron to carry out the oxidation of the organic material to produce carbon dioxide (e.g., by generating hydroxyl radicals and ozone on the surface of the boron doped diamond (BDD) electrode). The use of boron serves as a better electrode material than carbon-based or other metallic materials (e.g., silver, gold, mercury, nickel, etc.) because these materials poorly oxidize and may eventually themselves become oxidized. The O.I. TOC analyzer comprises one or more sensors capable of detecting carbon dioxide produced by the boron doped diamond electrode.

However, existing TOC analyzers utilizing BDD electrodes may fall short of measuring all of the oxidized carbon species. More particularly, hydroxyl radical oxidation of carbon species can produce two oxidation products, carbonate and oxalate, the proportion of which depends generally on the number of carbon atoms in the molecule (e.g., C1 (methanol) can only form carbonate (100%), C2 (ethanol) forms carbonate (~67%) and oxalate (~33%), etc.). Carbonate is measured in a $CO_2$ gas analyzer by acid addition that converts the carbonate into $CO_2$ gas. However, it is unclear whether current BDD TOC methods are able to completely measure the oxalate proportion, which may therefore result in an incomplete measurement (i.e., an underestimation of the total TOC content). Additionally, the lifespan of the thin film electrode is short because the thin film coating on the electrode suffers from delamination.

Advances in research have led to the discovery that adding a manganese catalyst, or other metallic catalyst, to a sample enables the oxalate to be converted to $CO_2$ gas, which can then be measured. However, these conventional methods still require the use of ozone to generate the active ingredient (i.e., the hydroxyl radical), which requires an expensive ozone generator. Additionally, the gas required for this technique is oxygen, which requires an oxygen concentrator in the analysis system.

Accordingly, an embodiment provides a method for oxidizing organic carbon in an aqueous solution and measuring the total organic carbon resulting from the oxidation process. In an embodiment, a fluid sample comprising organic carbon is introduced into a reaction chamber of a total organic carbon analyzer. The reaction chamber may comprise an electrochemical cell with a SP3 substituted carbon electrode doped with a conductivity elevating composition (e.g., boron, etc.). An embodiment may then apply a positive potential to the electrode to oxide any organics in the fluid sample to their corresponding oxidation process. An embodiment may then introduce a metallic catalyst (e.g., manganese, iron, nickel, chromium, another transition metal capable of oxidizing the organics in the fluid sample, etc.) to the fluid sample. These metallic catalysts will be oxidized to higher valent Mn (VII). These higher valent manganese species assist in the conversion of intermediate partially oxidized species (e.g., oxalate, etc.) to carbon dioxide which can then be detected and/or measured by at least one carbon dioxide detector/sensor. In this process Mn (VII) converts back to Mn(II). Such a method ensures complete recovery of all oxidized carbon species. Additionally, such a method has cost of production advantages over existing systems because, for example, an ozone generator would not be required and any sparge gas utilized could be air, not oxygen, which eliminates the requirement for an oxygen concentrator.

The illustrated example embodiments will be best understood by reference to the figures. The following description is intended only by way of example, and simply illustrates certain example embodiments.

Referring now to FIG. 1, an embodiment may measure the total organic carbon content present in an aqueous sample. At 101, an aqueous fluid sample containing organic carbon (e.g., water from a source, a solution containing a dissolved specimen, etc.) may be introduced into a TOC analyzer. In an embodiment, the TOC analyzer comprises an appropriate housing that is sealed to create a closed system in which carbon dioxide generated through an oxidation process cannot escape from the system prior to detection. In an embodiment, the housing comprises a reaction chamber that is configured to contain the aqueous fluid sample. The housing may also include a head space that may be configured to capture the gas-phase carbon dioxide.

In an embodiment, the reaction chamber may include an electrochemical cell. The electrochemical cell may comprise a plurality of electrodes (e.g., working electrode, reference electrode, counter electrode, etc.) in which the working electrode may be an SP3 substituted solid carbon electrode capable of oxidizing organics in an aqueous sample to produce carbon dioxide. In an embodiment, the SP3 substituted solid carbon electrode may be doped with a conductivity inducing material (e.g., boron, etc.) that is capable of raising the conductive band of the SP3 substituted solid carbon electrode. For simplicity purposes, the majority of the discussion herein will refer to boron as the conductivity inducing material, however, it should be understood that other suitable atoms capable of raising the conductive band of the SP3 substituted solid carbon electrode may also be used. In an embodiment, the electrode may be immersed in and be in contact with the sample aqueous fluid sample.

At 102, in an embodiment, a positive potential or positive current may be applied to the SP3 substituted solid carbon electrode. The potential or current may be applied using an electrical generator or other electrical power producing source (e.g., an external battery, etc.) to produce carbon dioxide at the surface of the SP3 substituted solid carbon electrode. In an embodiment the positive potential or current may be a potential or current large enough to sufficiently oxidize the organic compounds in the fluid sample to the oxidation products of carbonate and oxalate. For example, the electrical potential may be from 0.5-20 volts or electrical current from 0-20 A. In an embodiment, a galvanostat may be utilized to keep the current through the electrochemical cell constant.

In an embodiment, the oxidation process using the SP3 substituted solid carbon electrode may comprise the production of hydroxyl radicals by a one electron, one proton process in acidic/neutral media. The efficiency of the production of hydroxyl radical is dependent on the pH of the sample solution. More particularly, above pH 9 there is very little to no production of hydroxyl radicals. As such, in an embodiment, the pH may be maintained at ~1 to produce hydroxyl radicals electrochemically using one or more solid free standing SP3 substituted solid carbon electrodes. Thin film BDDs may undergo thermal stress because of the different thermal expansion coefficients between the substrate and BDD, which limits the current density that can be applied to these substrates. The SP3 substituted solid carbon electrode does not have the substrate and therefore the structural and electrical integrity may be maintained at a higher current. Such an embodiment may eliminate the need for adding alkaline solution and ozone, as is required in conventional methods. Additionally, the lack of substrate in the free standing SP3 substituted solid carbon electrode eliminates the problem of delamination that occurs on the thin-filmed BDD.

At 103, in an embodiment, at least one acid reagent comprising a metallic catalyst may be introduced into the sample in the reaction chamber. In an embodiment, the at least one acid reagent may react with any carbonate in the sample to produce carbon dioxide gas. In an embodiment, the same or different acid reagent may comprise a manganese (e.g., Mn (II)) catalyst. In an embodiment, regarding the Mn (II) catalyst, the pH of the sample solution may be maintained at acidic levels to oxidize the oxalate into carbon dioxide. The addition of the catalyst effectively ensures complete oxidation of the oxidation products to carbon dioxide.

At 104, in an embodiment, the carbon dioxide produced by the oxidation process may be measured. In an embodiment, the carbon dioxide may bubble into a same or separate collection chamber (e.g., the head space, etc.) where it can be measured using one or more sensors. In an embodiment, the head space may include a gas-phase detector (e.g., a carbon dioxide sensor, etc.) capable of measuring the amount of gas-phase carbon dioxide in the head space or in a separate chamber. In another embodiment, a liquid-phase detector (e.g., capable of measuring levels of dissolved carbon dioxide in the aqueous-phase, etc.) may be used in lieu of or in combination with the gas-phase detector to attain a complete measurement of the TOC in the sample. In an embodiment, the measured carbon dioxide may be substantially proportional to the amount of organic carbon present in the aqueous sample.

Figure 2:
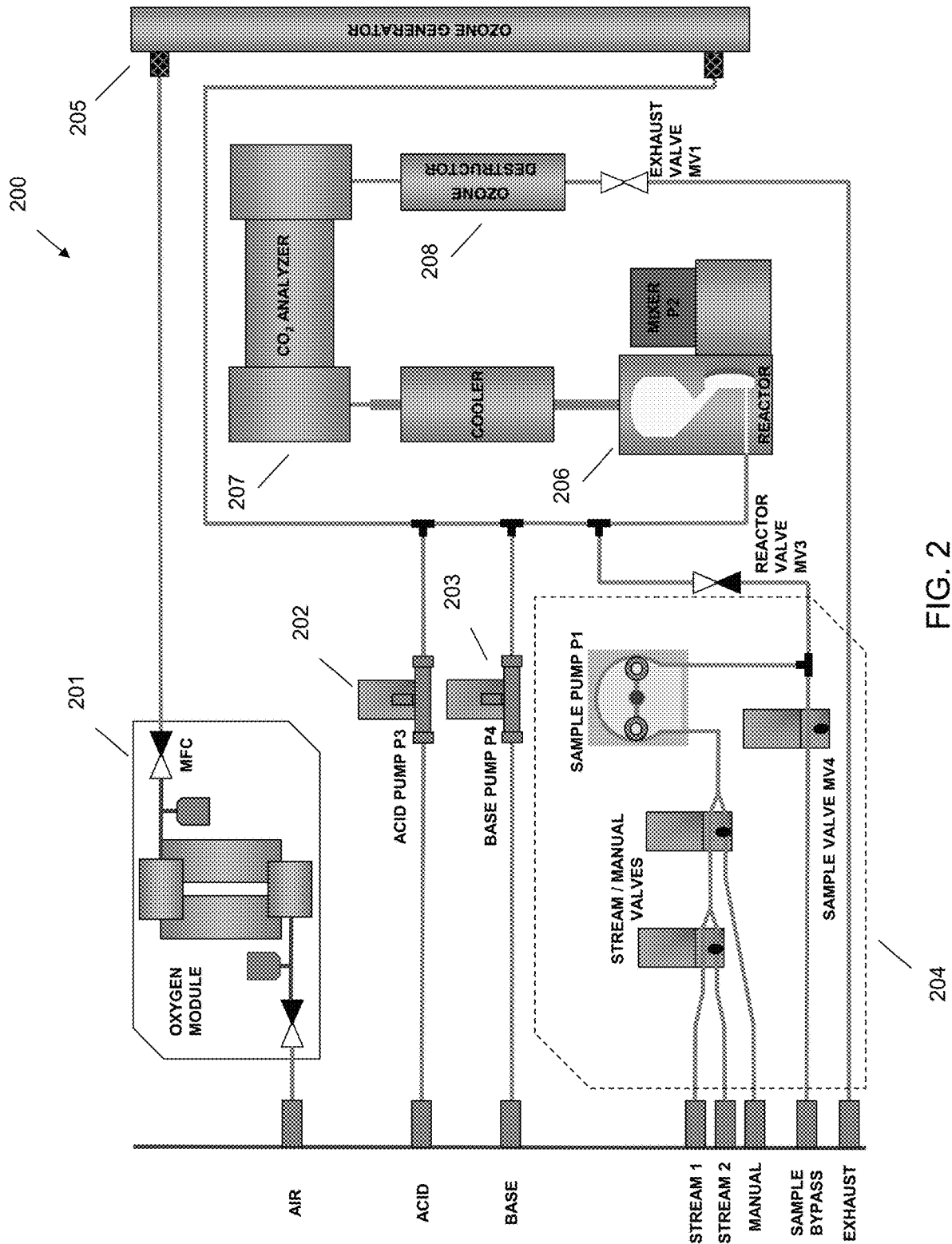
FIG. 2 illustrates a conventional TOC analyzer system.

FIG. 2 illustrates an example conventional analyzer system 200. The conventional system includes an oxygen module 201 which produces the sparge gas by using an oxygen concentrator to concentrate the oxygen from the air. The conventional system includes two reagent introduction mechanisms 202 and 203 which introduce an acid and base, respectively. The sample is introduced into the system using the sample electronics 204. The conventional system also includes an ozone generator 205 which produces ozone to be used in the reactor. The reagents, sample, and ozone are sent to the reactor 206 which mixes the sample. The reactor causes the production of the carbon which can then be measured with the $CO_2$ analyzer 207. The exhaust from the $CO_2$ analyzer 207 is then sent through an ozone destructor 208 before being exhausted.

Figure 3:
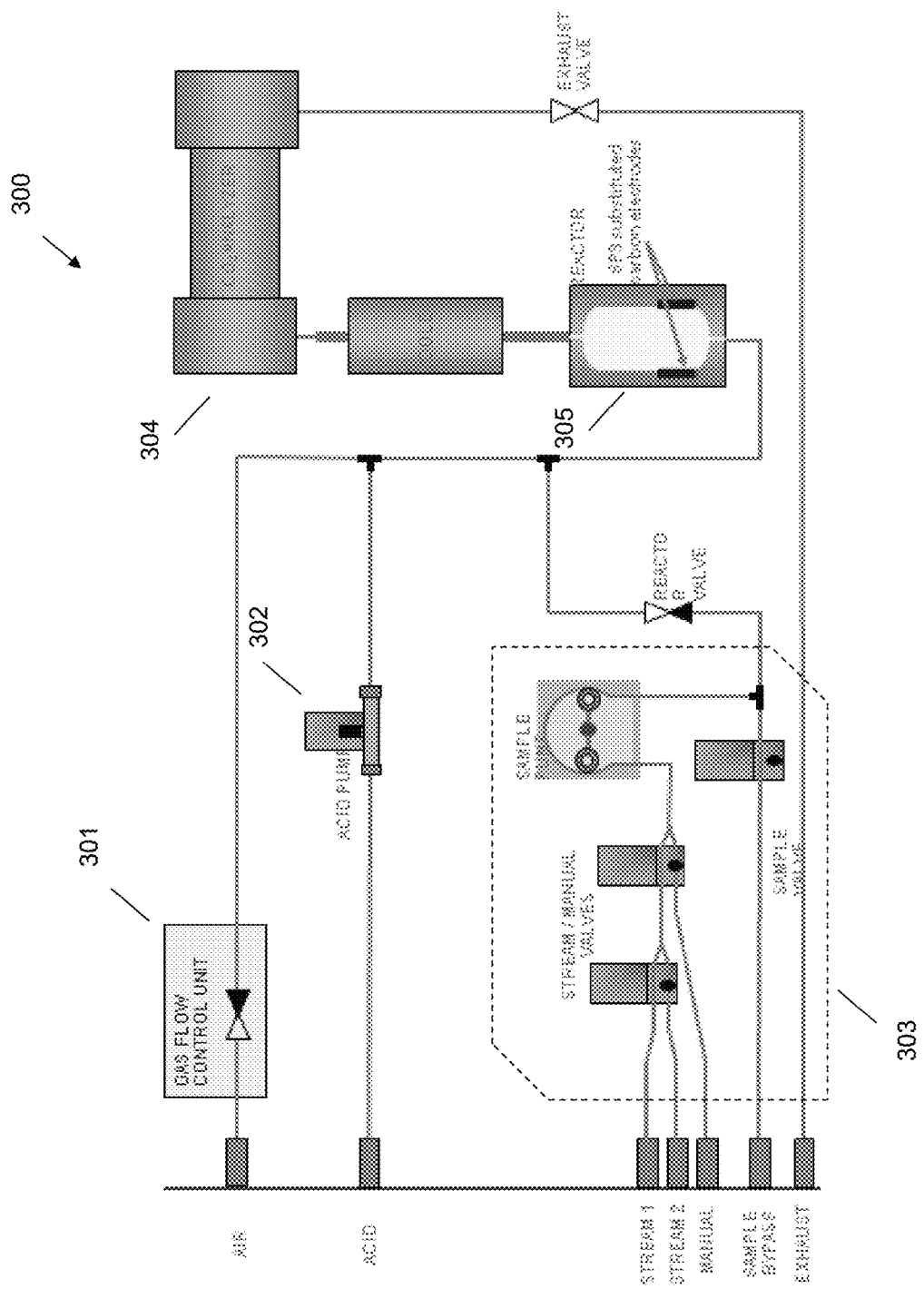
FIG. 3 illustrates an example SP3 substituted carbon electrode TOC analyzer according to an embodiment.

Using the system as described herein and illustrated in FIG. 3, the conventional analyzer system can be simplified. For example, an example embodiment of the system 300 as described herein can use air as the sparge gas, rather than oxygen. Accordingly, the oxygen module 201 can be removed and replaced with a gas flow control unit 301. Not only does this remove the large oxygen module 201, but it also reduces the amount of air that is required to generate the required oxygen of the conventional system. Additionally, only a single reagent is needed in the system 300 as described herein. Thus, one of the reagent pumps 202 and/or 203 can be removed from the system 300 (e.g., in FIG. 3 only the acid reagent pump 302 is present). The sample electronics 203 can also be simplified. The mixer portion of the reactor 206 can be removed and replaced with the SP3 substituted solid carbon electrodes 305 as described herein. Additionally, the system 300 as described herein does not require ozone. Therefore, both the large ozone generator 205 and the ozone destructor 208 can be removed. The system 300 as described herein may also result in a simpler $CO_2$ analyzer 207, which is shown as 304 in FIG. 3. Additionally, the system requires fewer and smaller components which results in a smaller overall housing.

Figure 4:
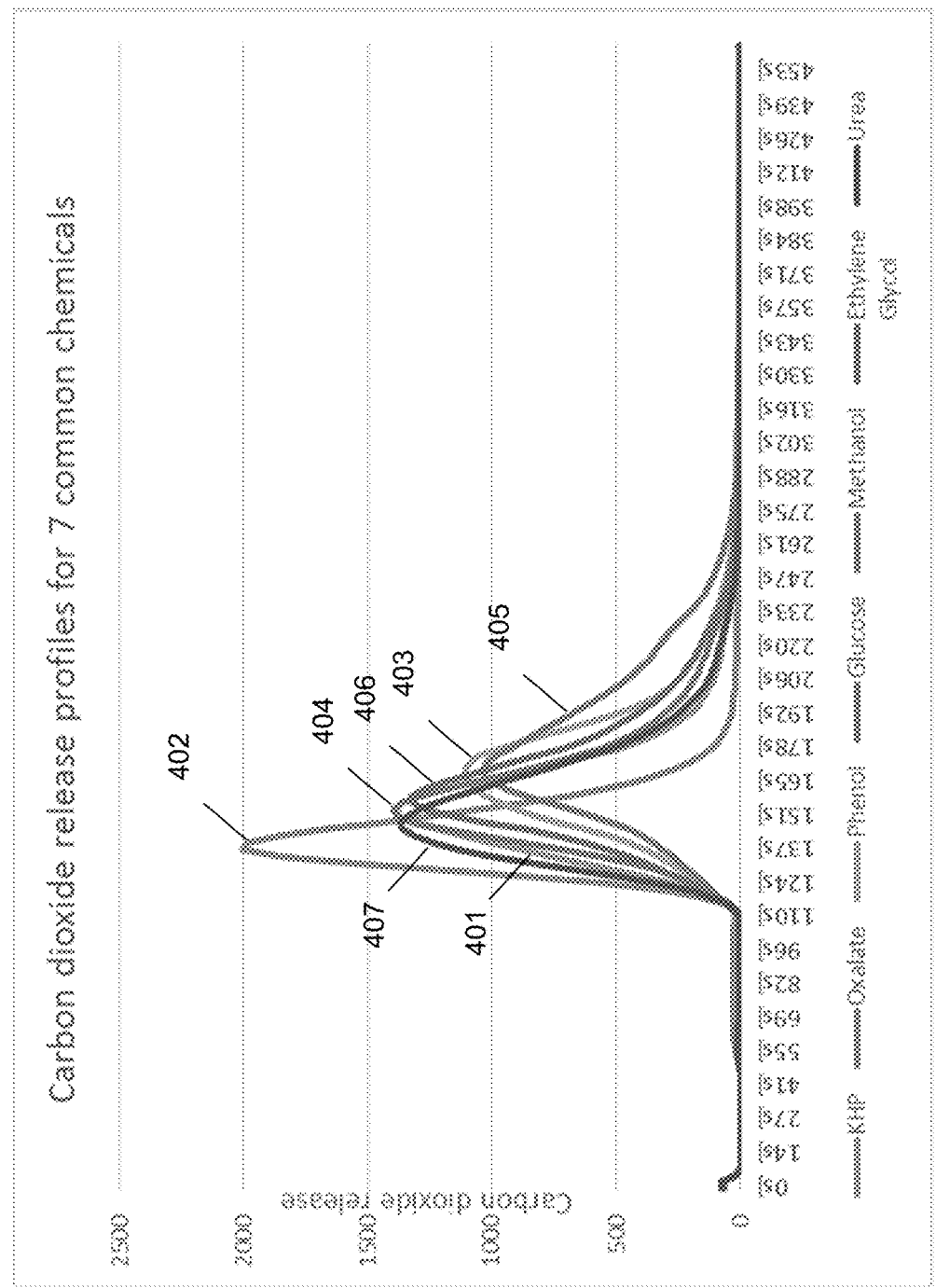
FIG. 4 illustrates an example graph illustrating recovery of common organics according to an embodiment.

Referring now to FIG. 4, carbon dioxide release profiles for seven common chemicals (i.e., KHP 401, Oxalate 402, Phenol 403, Glucose 404, Methanol 405, Ethylene Glycol 406, and Urea 407) are illustrated. These results were obtained using the first experimental SP3 substituted carbon electrode TOC analyser. Standards were 50 mgC/l and results were obtained by calculating the area under the curves for the individual chemicals. Included below is an example table of the results. Note that all results were between 47.9 and 51 mgC/l and that the high sharp peak is associated with oxalate, showing the fast response to the catalyst (manganese).

| Chemical | Result, mgC/l |
|---|---|
| KHP | 48.1 |
| Oxalate | 48.9 |
| Phenol | 47.9 |
| Glucose | 48.6 |
| Methanol | 50.1 |
| Ethylene Glycol | 49.5 |
| Urea | 51.0 |

The various embodiments described herein thus represent a technical improvement to conventional total organic carbon measuring techniques. Using the techniques described herein, an embodiment may receive a fluid sample containing organic carbon and oxidize the sample to produce the oxidation products carbonate and oxalate. An embodiment may then introduce an acid reagent and a metallic catalyst to the sample to convert the carbonate and partially oxidized species to carbon dioxide, which can then be measured. Such techniques provide a more accurate way of measuring the total organic carbon content in a sample and provide a more cost effective approach over existing methods.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a hand held measurement device such as illustrated in FIG. 1, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method, comprising:
    introducing, in a reaction chamber of a total organic carbon analyzer, a fluid sample comprising organic carbon, wherein the reaction chamber includes an electrochemical cell that comprises a thick-film SP3 substituted solid carbon electrode doped with a conductivity elevating composition, wherein the electrochemical cell is composed of a single compartment that does not include a cell-separating membrane;
    introducing, into the reaction chamber, air, wherein the air is obtained from a gas flow control unit;
    applying, using a generator, a positive potential to the thick-film SP3 substituted carbon electrode, the positive potential being sufficient to oxidize organics in the fluid sample to produce carbonate and partially oxidized organics, wherein the partially oxidized organics include oxalate;
    introducing, in the reaction chamber, at least one acid reagent comprising a metallic catalyst prior to or substantially simultaneously during the application of the positive potential to the thick-film SP3 substituted carbon electrode that converts, in a solid surface reaction, the carbonate and the partially oxidized species to carbon dioxide; and
    detecting, using a gas-phase carbon dioxide detector, the carbon dioxide produced by the oxidation;
    wherein the thick-film SP3 substituted carbon electrode is substrate-less and free-standing.

2. The method of claim 1, wherein the conductivity elevating composition comprises boron.

3. The method of claim 1, wherein the metallic catalyst is selected from the group consisting of manganese, iron, nickel, chromium, and another transition metal capable of oxidizing the organics in the fluid sample.

4. The method of claim 1, wherein the detecting comprises detecting, using the gas-phase carbon dioxide detector, bubbled carbon dioxide captured in a chamber of the total organic carbon analyzer.

5. The method of claim 1, further comprising measuring, using one or more spectrometers, the detected carbon dioxide produced by the oxidation.

6. The method of claim 1, wherein the applying comprises maintaining the positive potential at a substantially consistent current.

7. The method of claim 1, wherein the positive potential is selected from the range of 0.5 volts to 20 volts.

8. The method of claim 1, further comprising maintaining a pH level of the fluid sample at an acidic pH.

* * * * *